United States Patent
Igarashi et al.

(10) Patent No.: US 6,864,280 B2
(45) Date of Patent: Mar. 8, 2005

(54) γ-TOCOTRIENOL-CONTAINING DIURETICS

(75) Inventors: Osamu Igarashi, Tokyo (JP); Chikako Kiyose, Saitama (JP); Hiroyuki Yoshimura, Ibaraki (JP); Shigehiro Yoshitake, Nara (JP)

(73) Assignee: Eisai Co., Ltd., Tokyo (JP)

( * ) Notice: Subject to any disclaimer, the term of this patent is extended or adjusted under 35 U.S.C. 154(b) by 62 days.

(21) Appl. No.: 10/239,945

(22) PCT Filed: Mar. 27, 2001

(86) PCT No.: PCT/JP01/02479

§ 371 (c)(1),
(2), (4) Date: Sep. 24, 2002

(87) PCT Pub. No.: WO01/74354

PCT Pub. Date: Oct. 11, 2001

(65) Prior Publication Data

US 2003/0139467 A1 Jul. 24, 2003

(51) Int. Cl.$^7$ .............................................. A61K 31/355
(52) U.S. Cl. ........................................ 514/458; 514/456
(58) Field of Search ................................. 514/458, 456

(56) References Cited

FOREIGN PATENT DOCUMENTS

| EP | 0 669 132 | 8/1995 |
|---|---|---|
| JP | 10-506383 | 6/1998 |
| JP | 11-049 767 | 2/1999 |
| WO | 96/05191 | 2/1996 |
| WO | 99/06040 | 2/1999 |

OTHER PUBLICATIONS

Goodman & Gilman, The pharmacological basis of therapeutics, 5$^{th}$ edition, 1975, pp. 719–720.*

Newaz et al "Effect of γ–Tocotrienol on Blood Pressure, Lipid Peroxidation and Total Antioxidant Status in Spontaneously Hypertensive Rats (SHR)", *Clinical and Experimental Hypertension*, vol. 21, No. 8, Nov. 1999, pp. 1297–1313.

* cited by examiner

*Primary Examiner*—Rebecca Cook
(74) *Attorney, Agent, or Firm*—Flynn, Thiel, Boutell & Tanis, P.C.

(57) ABSTRACT

The present invention provides a diuretic, sodium ion-excreting agent, medicament for preventing or treating hypertension, medicament for preventing or treating ischemic cardiac diseases, medicament for preventing or treating congestive cardiac insufficiency or medicament for preventing or treating renal diseases, which comprises γ-tocotrienol.

11 Claims, 3 Drawing Sheets

γ-TOCOTRIENOL-CONTAINING DIURETICS

FIELD OF THE INVENTION

The present invention relates to a therapeutic agent, in particular to a diuretic, sodium ion-excreting agent etc., which comprises γ-tocotrienol.

PRIOR ART

γ-Tocotrienol is known to have a cholesterol-reducing action, a carotid artery stricture-preventing action, a breast cancer-preventing action, and an immune function-improving action (JP-A 11-49767). On the other hand, γ-CEHC (2,7,8-trimethyl-(S)-2-(β-carboxyethyl)-6-hydroxychroman, also called LLU-α), which is a metabolite of γ-tocopherol, is known to have a sodium diuresis action (JP-A 10-506383).

DISCLOSURE OF THE INVENTION

As the actions of γ-tocotrienol administered, the above-described cholesterol-reducing action, immune function-improving action etc. are known, and the present inventors studied a metabolite of γ-tocotrienol, and found that γ-tocotrienol has new actions described below, to complete the present invention.

The present invention provides a diuretic comprising γ-tocotrienol. Further, the present invention provides a sodium ion-excreting agent comprising γ-tocotrienol. Further, the present invention provides a medicament for preventing and treating hypertension, a medicament for preventing and treating ischemic cardiac diseases, a medicament for preventing and treating congestive cardiac insufficiency or a medicament for preventing and treating renal diseases, which comprises γ-tocotrienol.

The present invention provides a method for preventing or treating diseases in which a sodium ion-excreting is efficacious for the prevention or treatment, by administering a pharmacologically effective dose of γ-tocotrienol to a patient.

The present invention provides an use of γ-tocotrienol for producing a medicament for preventing or treating diseases in which a sodium ion-excreting is efficacious for the prevention or treatment.

In the present invention, the diseases in which a sodium ion-excreting is efficacious for the prevention or treatment include diseases in which a diuretic action is efficacious for the prevention or treatment, hypertension, ischemic cardiac diseases, congestive cardiac insufficiency and renal diseases.

In the present invention, γ-tocotrienol has a chemical name 2,7,8-trimethyl-2-(4,8,12-trimethyltrideca-3,7,11-trienyl)chroman-6-ol with the following structural formula:

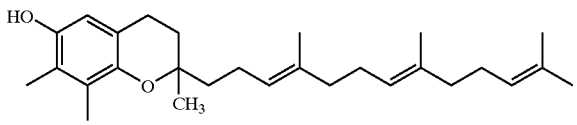

Tocotrienol can be obtained for example by extraction from vegetable oils such as palm oil, rice bran oil etc. or by chemical synthesis. Tocotrienol occurs as α-, β-, γ- and δ-isomers, any of which can be used in the present invention, but particularly γ-tocotrienol is preferable. Tocotrienol can be easily obtained as a commercial product.

Further, tocotrienol has intramolecular asymmetrical carbon atoms and a plurality of double bonds and can thus occur as optically active substances, racemic modifications or cis-isomer (Z-isomer), trans-isomer (E-isomer), cis-trans mixture (mixture of E and Z) etc. and as a combination of these substances, and any of such substances can be used without limitation in the present invention-. However, 2R-2, 7,8-trimethyl-2-(4,8,12-trimethyltrideca-3E, 7E, 11E-trienyl)chroman-6-ol can be mentioned as a more preferable example.

According to the present invention, excretion of sodium ion into urine is promoted and the volume of urine is increased upon administration of γ-tocotrienol into animals including humans. That is, it is effective on humans or animals.

The pharmaceutical preparation according to the present invention is administered orally or parenterally. For oral administration, it can be generally formed into pharmaceutical forms such as tablets, powders, granules, capsules, liquids and troches. To prepare these pharmaceutical forms, generally used pharmaceutical manufacturing assistants and pharmaceutical manufacturing methods can be used. For example, as fillers, lactose, mannitol, xylitol, erythritol, crystalline cellulose, calcium hydrogen phosphate, light silicic anhydride etc.; as disintegrating agents, carboxymethyl cellulose calcium, low-substituted hydroxypropyl cellulose, starch, cross carmerose sodium etc.; as binders, hydroxypropyl cellulose, hydroxypropylmethyl cellulose, polyvinyl pyrrolidone etc.; and as lubricants, stearic acid, calcium stearate, magnesium stearate etc. may be proposed. Further, it is also possible to use coloring agents such as sesquioxide and tar type coloring matter.; and surfactants such as polyoxyethylene hardened castor oil, sucrose fatty ester, sorbitan fatty ester and Macrogol. Since tocotrienol is a substance liable to oxidation, it is particularly preferable to add a small amount of antioxidants such as tocopherol, dibutylhydroxy toluene, propyl gallate etc.

Further, for parenteral administration, it can be prepared in pharmaceutical forms such as injections, suppositories, ointments, nasal sprays etc. Tocotrienol is an oily substance, so that for preparing injections, it is emulsified or solubilized by adding surfactants such as polyoxyethylene hardened castor oil, sucrose fatty ester, sorbitan fatty ester, Macrogol etc. and as necessary sorbitol, mannitol etc. to regulate the osmotic pressure and buffers to adjust the pH. The dose of γ-tocotrienol is varied depending on the administration route and not determined unconditionally, but for oral administration, the daily dose is usually 0.01 to 10 g, preferably 0.03 to 5 g, more preferably 0.03 to 1 g. γ-Tocotrienol is a very safe substance, and its severe side effects upon administration are not known.

Figure 1:
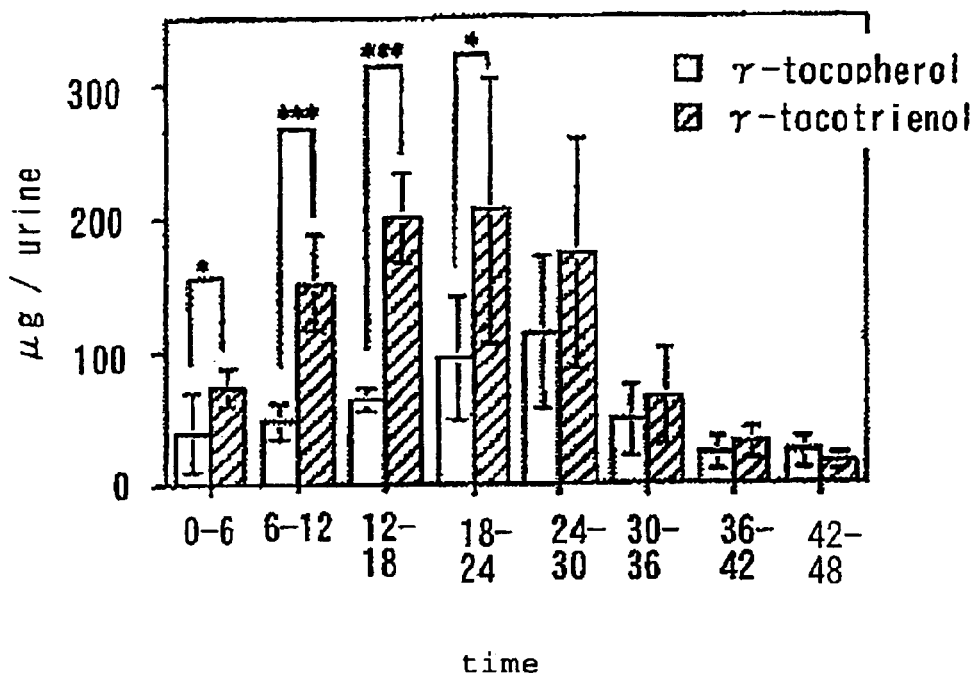
FIG. 1 is a graph showing the amounts of γ-CEHC excreted in urine with time (mean±standard deviation, n=3 or 4, *: p<0.05, ***: p<0.001 (t-test)).

The effects of the present invention are described in the following Experimental Examples.

PHARMACOLOGICAL EXPERIMENTAL EXAMPLE 1

Change in the Amount of γ-CEHC Excreted by γ-Tocotrienol

Methods

1. Experimental Animals

Seven-week-old Sprague-Dawley strain male rats, purchased from Nippon Clare Co., Ltd., were preliminarily bred with solid feed CE-2 (Nippon Clare Co., Ltd.) for 1 week and then bred with vitamin E-deficient feed for 4 weeks. The rats were placed in a stainless steel cage/rat, and the breeding room was maintained at a temperature of 22±1° C. in 50% humidity. The animals were allowed feed and water ad libitum.

2. Feed

The feed was prepared by adding 10% corn oil (stripped corn oil) from which vitamin E had been removed by molecular distillation, to vitamin E-deficient powdery feed.

3. Experimental Protocol

The bred vitamin E-deficient-rats were divided into 2 groups and fasted for 17 hours, and each rat in one group was orally given 10 mg/0.5 ml γ-tocotrienol dissolved in stripped corn oil, while as the control, each rat in the other group was orally given 10 mg/0.5 ml γ-tocopherol in analogous manner. After the administration, the rats in a urine collection group were placed in a metabolic cage/rat, and their urine was collected at 6-hours intervals for 48 hours during which a collection vessel was cooled on dry ice. The rats in a bile collection group were anesthetized with Nembutal in 2 hours after the administration in consideration of absorption time, and the abdomens of the rats were opened with their back fixed under anesthesia and a canula was inserted into the bile duct. As the canula, a polyethylene tube (Natsume Seisakusho) was used, and after the inserted canula was fixed so as not to be removed, the abdomens were sutured. After the operation, intraperitoneal administration of Nembutal into the rats with the back fixed was conducted for anesthesia whenever necessary until the experiment was finished. The bile was collected in collection vessels cooled on dry ice for 24 hours after the administration, that is, in 3 hours and in 6 hours after the administration and thereafter at 6-hours intervals. After the collection, the urine and bile were immediately freeze-dried and stored at −20° C. until measurement.

4. Method of Measuring γ-CEHC in the Urine and Bile

In pre-treatment, the urine powder and the bile powder were re-dissolved in 10 ml and 5 ml purified water respectively, then 0.5 ml and 0.1 ml aliquots were taken from the solutions respectively, and 1 ml of 0.54 mM EDTA was added thereto, followed by stirring. Thereafter, 1 ml of 10% ascorbic acid solution was added thereto, and each mixture was stirred, frozen at −80° C. and freeze-dried. To the resulting sample powder was added 2 ml of 3N methanolic hydrochloric acid, and the sample was methylated at 60° C. for 1 hour under nitrogen. Thereafter, 6 ml water was added thereto and the product was extracted with 3 ml hexane. The hexane layer (2 ml) was collected, and the solvent was removed, and the residue was re-dissolved in 45% aqueous acetonitrile containing 50 mM sodium perchlorate and then injected into HPLC. In this procedure, the urine sample and the bile sample were dissolved in 4 ml and 2 ml of the aqueous acetonitrile, respectively. For calculation of the amount of γ-CEHC in each sample, the external standard method was used.

Results

Figure 2:
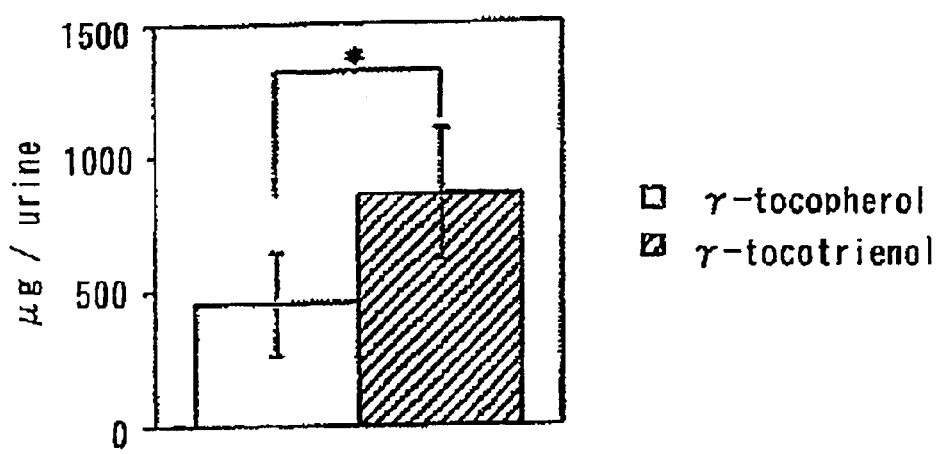
FIG. 2 is a graph showing the amounts of γ-CEHC excreted in urine for 48 hours (mean±standard deviation, n=3 or 4, *: p<0.05 (t-test)).

The results are shown in FIGS. 1 and 2. FIG. 1 is a graph showing the amount of γ-CEHC excreted in urine with time after administration of γ-tocotrienol or γ-tocopherol. It is evident that the amount of γ-CEHC excreted in urine in the group given γ-tocotrienol is higher for a period of up to 42 hours after administration than in the group given γ-tocopherol. FIG. 2 shows the amount of γ-CEHC excreted in urine for a period of up to 48 hours after administration of γ-tocotrienol or γ-tocopherol. It is evident that the amount of γ-CEHC excreted in urine in the group given γ-tocotrienol is significantly higher than in the group given γ-tocopherol. It is known that γ-CEHC has a sodium ion-excreting action and a diuresis action. On the other hand, it is known that γ-CEHC is formed as a metabolite of γ-tocopherol.

From this experiment, it is evident that upon administration of γ-tocotrienol, γ-CEHC was excreted, that is, γ-CEHC was formed in vivo, and a larger amount of γ-CEHC excreted than after administration of tocopherol means that a larger amount of γ-CEHC was formed in vivo upon administration of γ-tocotrienol. This indicates that administration of γ-tocotrienol, as compared with administration of γ-tocopherol in the same amount, is equivalent to administration of a larger amount of γ-CEHC having a diuresis action. Thus, γ-tocotrienol is shown to be superior as a diuretic to γ-tocopherol.

Figure 3:
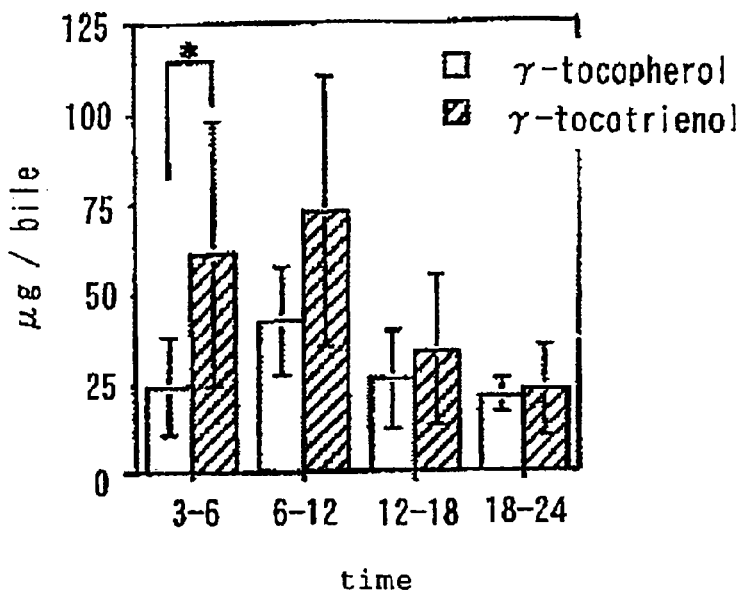
FIG. 3 is a graph showing the amounts of γ-CEHC excreted in bile with time (mean±tandard deviation, n=3~5, *: p<0.05 (t-test)).

The in vivo formation of γ-CEHC upon administration of γ-tocotrienol is also evident from the excretion of γ-CEHC into the bile as shown in FIG. 3. Since γ-CEHC excreted into the bile is larger in the group given γ-tocotrienol than in the group given γ-tocopherol, it is suggested that γ-CEHC is formed in vivo in a larger amount in the group given γ-tocotrienol than in the group given γ-tocopherol.

PHARMACOLOGICAL EXPERIMENTAL EXAMPLE 2

Effect of γ-Tocotrienol on Excretion of Sodium into Urine

Method

Seven-week-old SD strain male rats (n=20) were preliminarily bred with solid feed and divided into 2 groups. One group was given vitamin E-deficient feed (AIN-76) and used as a control group. The other group was given high-salt feed prepared by adding 5% common salt to 1 kg vitamin E-deficient feed and used as a group given high-salt (high-Na) feed. Each animal in both the groups was given 20 g feed/day for 1 week and 25 g feed/day during a period of from the second to fourth weeks. 150 ml of purified water was given as drinking water, and the remainder of the water was measured. After 4 weeks, each group was further divided into 2 groups, and each rat in one group was given 10 mg γ-tocotrienol (control+γ-tocotrienol, High-Na+γ-tocotrienol) dissolved in stripped corn oil while the other group i.e. the control was given stripped corn oil (control, High-Na) for 3 consecutive days respectively, and after administration, their urine, while being frozen on dry ice, was collected at 6-hours intervals for 24 hours. The amounts of sodium and potassium in the urine were determined by the atomic absorption method and the amount of γ-CEHC by the ECD-HPLC method.

Results

Figure 4:
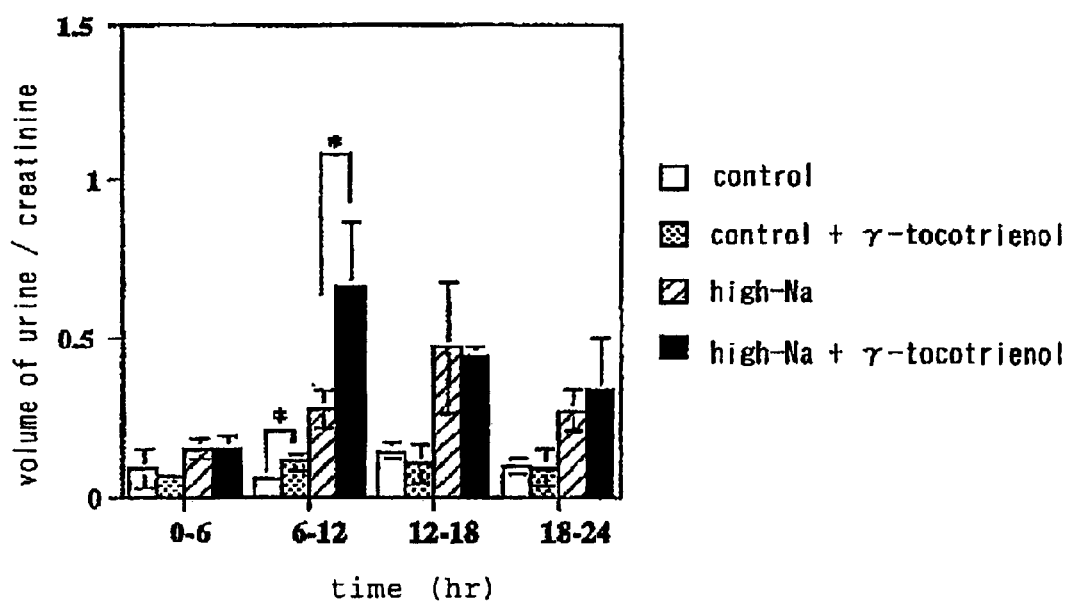
FIG. 4 is a graph showing a change with time in the volumes of urine, corrected with creatinine (mean±standard deviation, n=4, *: p<0.05 (t-test)).

1. Change in the Volume of Urine (see FIG. 4)

As to the change in the volume of urine after the administration, it tended to be larger in the groups given the high-salt feed, regardless of whether γ-tocotrienol was administered or not. In the groups given the high-salt feed, the urine volume tended to be larger in the group given γ-tocotrienol, and it was significantly increased for 6 to 12 hours after the administration.

2. Change in the Amount of Sodium Excreted (see FIG. 5)

Figure 5:
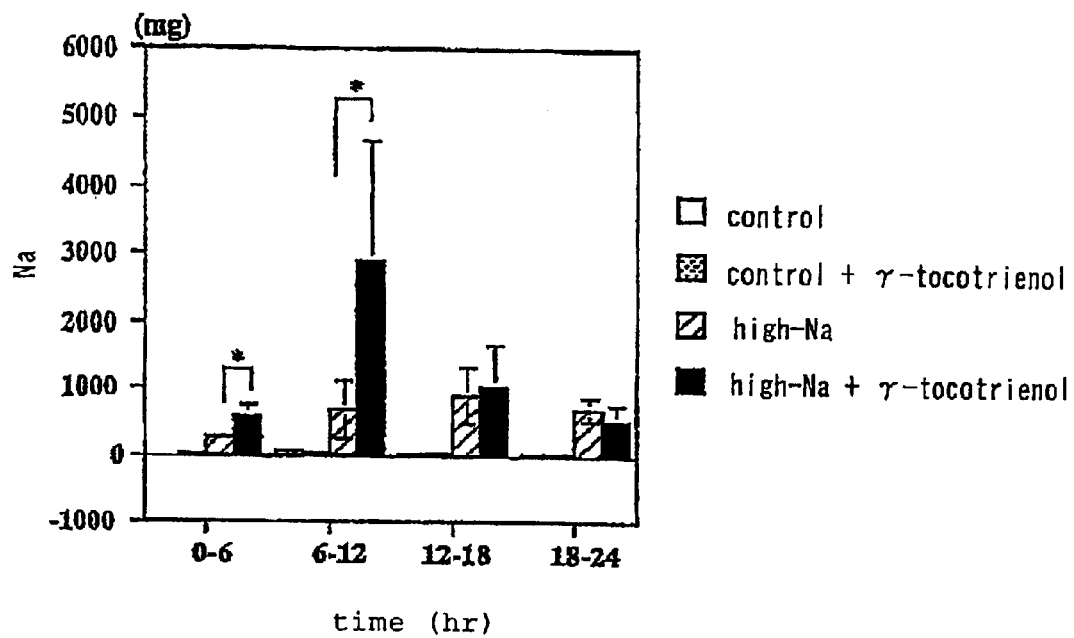
FIG. 5 is a graph showing a change with time in the amounts of sodium excreted in urine (mean±standard deviation, n=4, *: p<0.05 (t-test)).

The change in the amount of sodium excreted is shown in FIG. 5. This graph shows the amount of sodium excreted for the corresponding time. As a result, particularly in the high-salt group, those rats to which γ-tocotrienol had been administered showed a significantly larger amount of excreted sodium for a period of up to 12 hours after the administration. From these results, it was suggested that administration of γ-tocotrienol to those animals given the high-salt feed promotes excretion of sodium, and this effect was estimated to appear at a considerable early stage after the administration.

3. Influence on Potassium Excretion (see FIG. 6)

Figure 6:
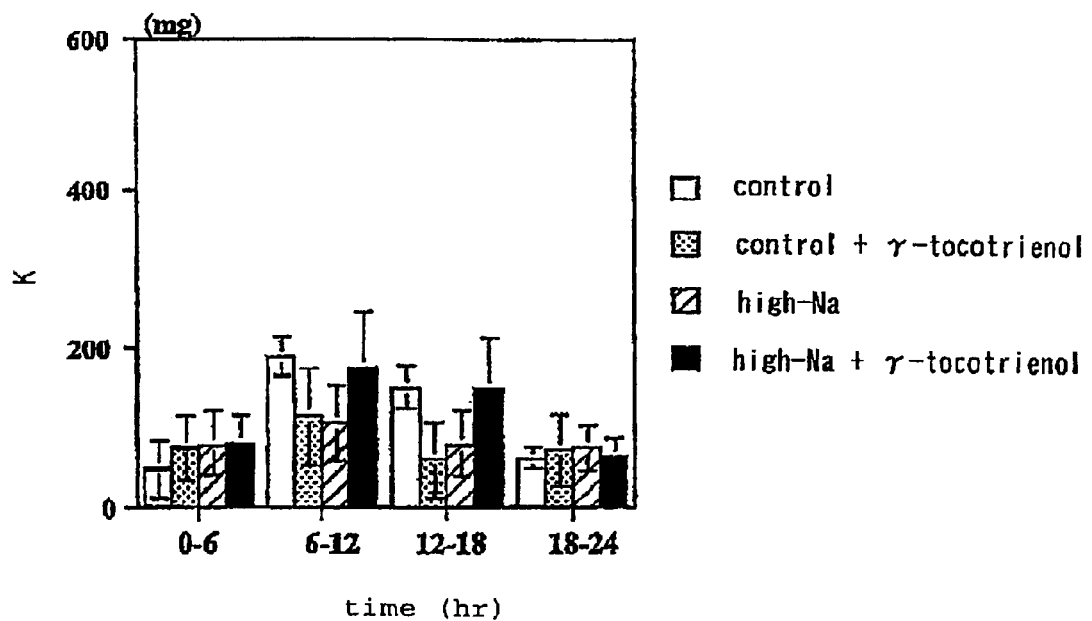
FIG. 6 is a graph showing a change with time in the amounts of potassium excreted in urine (mean±standard deviation, n=4)

The change in the amount of potassium excreted is shown in FIG. 6. There is no difference in the amount of excreted potassium among the 4 groups, and accordingly, the influence of γ-tocotrienol administration was not observed.

From the results described above, it was suggested that γ-tocotrienol promotes excretion of sodium into urine particularly upon ingestion of high salt, but does not influence potassium excretion, and this effect was estimated to appear at an early stage after the administration.

As described in detail above, the fact that γ-tocotrienol has a sodium ion-excreting action and a diuresis action indicates that γ-tocotrienol also serves as a medicament for preventing or treating hypertension, medicament for preventing or treating ischemic cardiac diseases, medicament for preventing or treating congestive cardiac insufficiency or medicament for preventing or treating renal diseases.

Tocotrienol as compared with tocopherol is structurally characterized by having double bonds in the side chain. γ-CEHC is a compound derived from γ-tocopherol by cleaving and shortening the side chain while maintaining the chroman ring, so it is considered that the side chain on γ-tocotrienol is more rapidly cleaved in vivo to form a larger amount of γ-CEHC.

What is claimed is:

1. A method of treating a disease in which sodium ion excretion is efficacious in the treatment of the disease comprising administering to a subject in which the disease is to be treated an amount of γ-tocotrienol effective to excrete sodium ion.

2. A method of treating disease in which a diuretic activity is efficacious in the treatment of the disease, comprising administering to a subject in which the disease is to be treated an amount of γ-tocotrienol effective to effect diuretic activity.

3. A method of inducing diuresis in a subject comprising a step of administering to aid subject a pharmacologically effective amount of γ-tocotrienol.

4. The method of claim 1, wherein said disease is at least one disease selected from the group consisting of hypertension, an ischemic cardiac disease, congestive cardiac insufficiency and a renal disease.

5. The method of claim 2, wherein said disease is at least one disease selected from the group consisting of hypertension, an ischemic cardiac disease, congestive cardiac insufficiency and a renal disease.

6. The method of claim 1, wherein the γ-tocotrienol is administered orally or parenterally.

7. The method of claim 2, wherein the γ-tocotrienol is administered orally or parenterally.

8. The method of claim 3, wherein the γ-tocotrienol is administered orally or parenterally.

9. The method of claim 1, wherein the γ-tocotrienol is administered in a daily dose of from 0.01–10 grams.

10. The method of claim 2, wherein the γ-tocotrienol is administered in a daily dose of from 0.01–10 grams.

11. The method of claim 3, wherein the γ-tocotrienol is administered in a daily dose of from 0.01–10 grams.

* * * * *

UNITED STATES PATENT AND TRADEMARK OFFICE
CERTIFICATE OF CORRECTION

PATENT NO. : 6,864,280 B2  Page 1 of 1
DATED : March 8, 2005
INVENTOR(S) : Igarashi et al.

It is certified that error appears in the above-identified patent and that said Letters Patent is hereby corrected as shown below:

Column 6,
Line 15, change from "administering to aid subject" to -- administering to said subject --.

Signed and Sealed this

Twelfth Day of July, 2005

JON W. DUDAS
*Director of the United States Patent and Trademark Office*